United States Patent
Miesak et al.

(10) Patent No.: US 9,390,309 B2
(45) Date of Patent: Jul. 12, 2016

(54) LATENT FINGERPRINT DETECTORS AND FINGERPRINT SCANNERS THEREFROM

(71) Applicant: LOCKHEED MARTIN CORPORATION, Bethesda, MD (US)

(72) Inventors: Edward Miesak, Windermere, FL (US); V. Edward Gold, Jr., Belle Isle, FL (US)

(73) Assignee: LOCKHEED MARTIN CORPORATION, Bethesda, MD (US)

( * ) Notice: Subject to any disclaimer, the term of this patent is extended or adjusted under 35 U.S.C. 154(b) by 53 days.

(21) Appl. No.: 14/333,720

(22) Filed: Jul. 17, 2014

(65) Prior Publication Data

US 2015/0317505 A1 Nov. 5, 2015

Related U.S. Application Data

(60) Division of application No. 13/976,177, filed as application No. PCT/US2011/059008 on Nov. 2, 2011, now Pat. No. 8,805,033, which is a continuation of application No. 13/049,351, filed on Mar. 16, 2011, now Pat. No. 8,437,517.

(60) Provisional application No. 61/409,753, filed on Nov. 3, 2010.

(51) Int. Cl.
*G06K 9/00* (2006.01)
*G06K 7/00* (2006.01)
(Continued)

(52) U.S. Cl.
CPC ........ *G06K 9/00033* (2013.01); *G01N 21/8851* (2013.01); *G01N 21/94* (2013.01);
(Continued)

(58) Field of Classification Search
USPC ..................................... 382/124, 312; 356/71
See application file for complete search history.

(56) References Cited

U.S. PATENT DOCUMENTS

| 4,120,585 A | 10/1978 | DePalma et al. |
| 4,247,784 A | 1/1981 | Henry |

(Continued)

FOREIGN PATENT DOCUMENTS

| CN | 2603449 | 2/2004 |
| CN | 201210214 | 3/2009 |

(Continued)

OTHER PUBLICATIONS

Lin et al, "Polarization and Specular-Reflection-Based, Non-contact Latent Fingerprint Imaging and Lifting", 2006, Journal of the Optical Society of America A, vol. 23, Issue 9, pp. 2137-2153.*

(Continued)

*Primary Examiner* — Kathleen Y Dulaney
(74) *Attorney, Agent, or Firm* — Terry M. Sanks, Esq.; Beusse Wolter Sanks & Maire, PLLC

(57) ABSTRACT

This document relates to systems and method for latent fingerprint detection using specular reflection (glare). An exemplary system may include a light source alignment portion configured to align a light source at an illumination angle relative to a sample surface such that the light source illuminates a sample surface so that the surface produces specular reflection. The system may also include a specular reflection discriminator that directs the produced specular refection to an optical detector aligned relative to said sample surface at an alignment angle that is substantially equal to an angle of reflection of the produced specular reflection. Preferably, the directed specular reflection does not saturate the optical detector, and the optical detector captures the specular reflection from the sample surface and generates image data using essentially only the specular reflection.

15 Claims, 10 Drawing Sheets

(51) Int. Cl.
*G06K 9/74* (2006.01)
*G01N 21/88* (2006.01)
*G06K 9/20* (2006.01)
*G01N 21/94* (2006.01)

(52) U.S. Cl.
CPC .......... *G06K9/00013* (2013.01); *G06K 9/2036* (2013.01); *G01N 2201/06113* (2013.01); *G01N 2201/10* (2013.01)

(56) References Cited

U.S. PATENT DOCUMENTS

| | | |
|---|---|---|
| 4,351,588 A | 9/1982 | Zullig |
| 4,632,807 A | 12/1986 | Marsoner |
| 4,783,167 A | 11/1988 | Schiller et al. |
| 4,785,171 A | 11/1988 | Dowling, Jr. et al. |
| 4,989,968 A | 2/1991 | Freedman |
| 5,004,349 A | 4/1991 | Sato et al. |
| 5,099,131 A | 3/1992 | Brownrigg et al. |
| 5,109,427 A | 4/1992 | Yang |
| 5,123,723 A | 6/1992 | Chesnutt et al. |
| 5,210,588 A | 5/1993 | Lee |
| 5,233,404 A | 8/1993 | Lougheed et al. |
| 5,266,805 A | 11/1993 | Edgar |
| 5,313,265 A * | 5/1994 | Hayes ............... G01B 9/02064 356/511 |
| 5,629,764 A | 5/1997 | Bahuguna et al. |
| 5,720,772 A | 2/1998 | Eckhouse |
| 5,812,252 A * | 9/1998 | Bowker ............... F41A 17/066 250/227.11 |
| 5,912,768 A * | 6/1999 | Sissom ............... G01B 11/026 359/625 |
| 5,963,657 A | 10/1999 | Bowker et al. |
| 6,005,963 A * | 12/1999 | Bolle ............... G06K 9/00067 382/115 |
| 6,115,484 A | 9/2000 | Bowker et al. |
| 6,124,238 A | 9/2000 | Chapman et al. |
| 6,127,189 A | 10/2000 | Joullie et al. |
| 6,144,453 A * | 11/2000 | Hallerman ......... G01N 21/8806 356/616 |
| 6,193,425 B1 | 2/2001 | Edgar |
| 6,292,576 B1 | 9/2001 | Brownlee |
| 6,354,724 B1 | 3/2002 | Sakashita |
| 6,488,892 B1 * | 12/2002 | Burton ............... B01L 9/523 356/244 |
| 6,503,695 B1 | 1/2003 | Miyazawa et al. |
| 6,558,052 B2 | 5/2003 | Edgar |
| 6,643,390 B1 * | 11/2003 | Clark ............... G06K 9/00046 356/71 |
| 6,665,427 B1 * | 12/2003 | Keagy ............... G06K 9/00046 382/124 |
| 6,668,071 B1 | 12/2003 | Minkin et al. |
| 6,885,017 B2 | 4/2005 | Lee et al. |
| 6,989,547 B2 | 1/2006 | Lee et al. |
| 6,995,384 B2 | 2/2006 | Lee et al. |
| 7,039,224 B2 | 5/2006 | Hamid et al. |
| 7,181,052 B2 | 2/2007 | Fujieda |
| 7,212,330 B2 | 5/2007 | Seo et al. |
| 7,234,641 B2 | 6/2007 | Olmstead |
| 7,295,688 B2 | 11/2007 | Hara et al. |
| 7,346,200 B1 | 3/2008 | Tsipouras et al. |
| 7,420,663 B2 | 9/2008 | Wang et al. |
| 7,489,391 B2 * | 2/2009 | Engheta ............... A61B 5/1172 356/71 |
| 7,787,110 B2 | 8/2010 | Raguin et al. |
| 7,846,191 B2 | 12/2010 | Vaynberg et al. |
| 8,077,929 B2 | 12/2011 | Heidt |
| 8,180,120 B2 | 5/2012 | Hook |
| 8,371,695 B2 | 2/2013 | Papac et al. |
| 8,396,319 B2 * | 3/2013 | Pugh, Jr. ............... 348/254 |
| 8,437,517 B2 | 5/2013 | Miesak et al. |
| 8,805,033 B2 | 8/2014 | Miesak et al. |
| 9,188,546 B2 | 11/2015 | Miesak et al. |
| 2003/0118219 A1 | 6/2003 | Higuchi et al. |
| 2003/0156284 A1 * | 8/2003 | Farr ............... G01J 3/02 356/326 |
| 2003/0156740 A1 * | 8/2003 | Siegel ............... G06F 21/10 382/115 |
| 2003/0185425 A1 * | 10/2003 | Nishikawa ......... G06K 9/00026 382/124 |
| 2004/0026635 A1 | 2/2004 | Lee et al. |
| 2005/0141756 A1 * | 6/2005 | Lee ............... G06K 9/00013 382/124 |
| 2006/0008129 A1 | 1/2006 | Lee et al. |
| 2006/0120573 A1 | 6/2006 | Iori |
| 2007/0177233 A1 * | 8/2007 | Ichikawa ............ H04N 1/00795 358/509 |
| 2007/0201733 A1 | 8/2007 | Hara |
| 2009/0052752 A1 * | 2/2009 | Monden ............... G06K 9/036 382/124 |
| 2009/0155456 A1 | 6/2009 | Benkley et al. |
| 2010/0303311 A1 * | 12/2010 | Shin ............... G06K 9/036 382/124 |
| 2010/0311005 A1 * | 12/2010 | Liang ............... A61B 1/00009 433/29 |
| 2011/0076383 A1 | 3/2011 | Reedy et al. |
| 2011/0121758 A1 | 5/2011 | Bierhuizen et al. |
| 2012/0105586 A1 | 5/2012 | Miesak et al. |
| 2012/0138728 A1 | 6/2012 | Brunton et al. |
| 2013/0301887 A1 | 11/2013 | Miesak et al. |
| 2014/0254894 A1 | 9/2014 | Miesak et al. |
| 2015/0317505 A1 | 11/2015 | Miesak et al. |
| 2015/0338745 A1 | 11/2015 | Fukazawa |
| 2016/0026845 A1 | 1/2016 | Miesak et al. |

FOREIGN PATENT DOCUMENTS

| | | |
|---|---|---|
| JP | 05-220131 | 8/1993 |
| JP | 06-147852 | 5/1994 |
| JP | 2001034738 | 2/2001 |
| WO | 2006073450 | 7/2006 |
| WO | 2010064034 | 6/2010 |
| WO | 2010071215 | 6/2010 |

OTHER PUBLICATIONS

Seto, Eileen K. et al., "Imaging Electrophoretic Gels with a Scanning Beam Lasser Macroscope," Electrophoresis, Wiley Interscience, DE, Apr. 15, 2005, pp. 934-940, vol. 16.

"Chapter 2: Finger Mark Examination Techniques within Scope of ISO 17025 2.1 Visual Examination," Mar. 26, 2013, pp. 291-293, XP055130668.

James Robertson, 2004 by CRC Press LLC, "The Practice of Crime Scene Investigation" (pp. 1-424).

Bartick et al., 2002, "Spectrochemical Analysis and Hyperspectral Imaging of Latent Fingerprints" (pp. 61-64).

Austin Richards, Mar. 28, 2010, "Reflected Ultraviolet Imaging for Forensics Applications" (pp. 1-31).

Tahtouh et al., 2005, "The Detection and Enhancement of Latent Fingermaks Using Infrared Chemical Imaging" (pp. 1-9).

Forensic Lab 8.0: Revealing Latent Fingerprints—Introduction, Aug. 16, 2009, pp. 1-17.

* cited by examiner

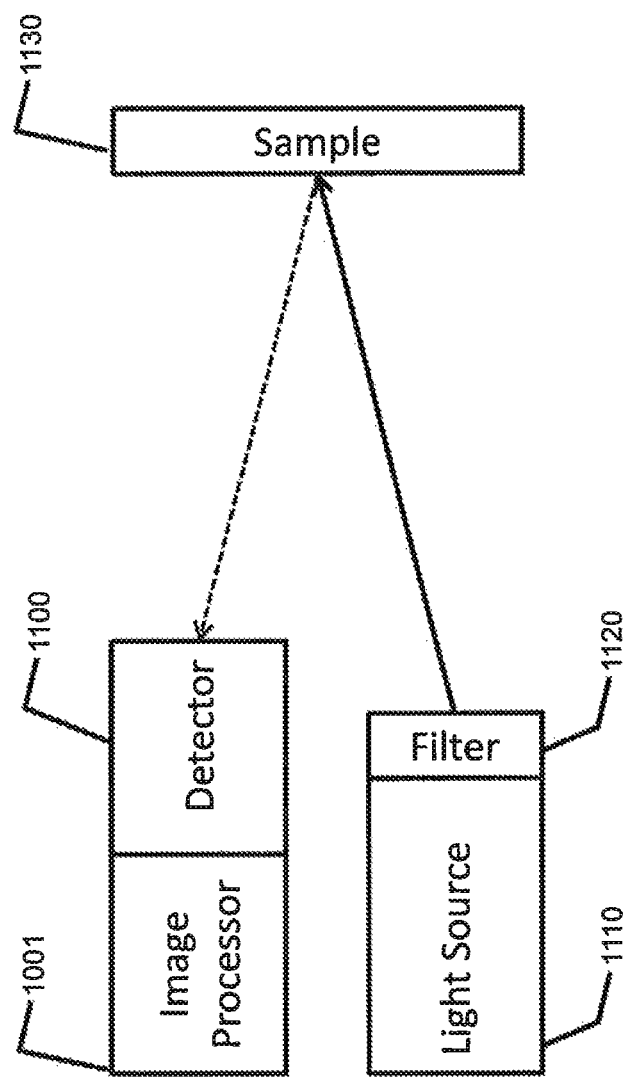

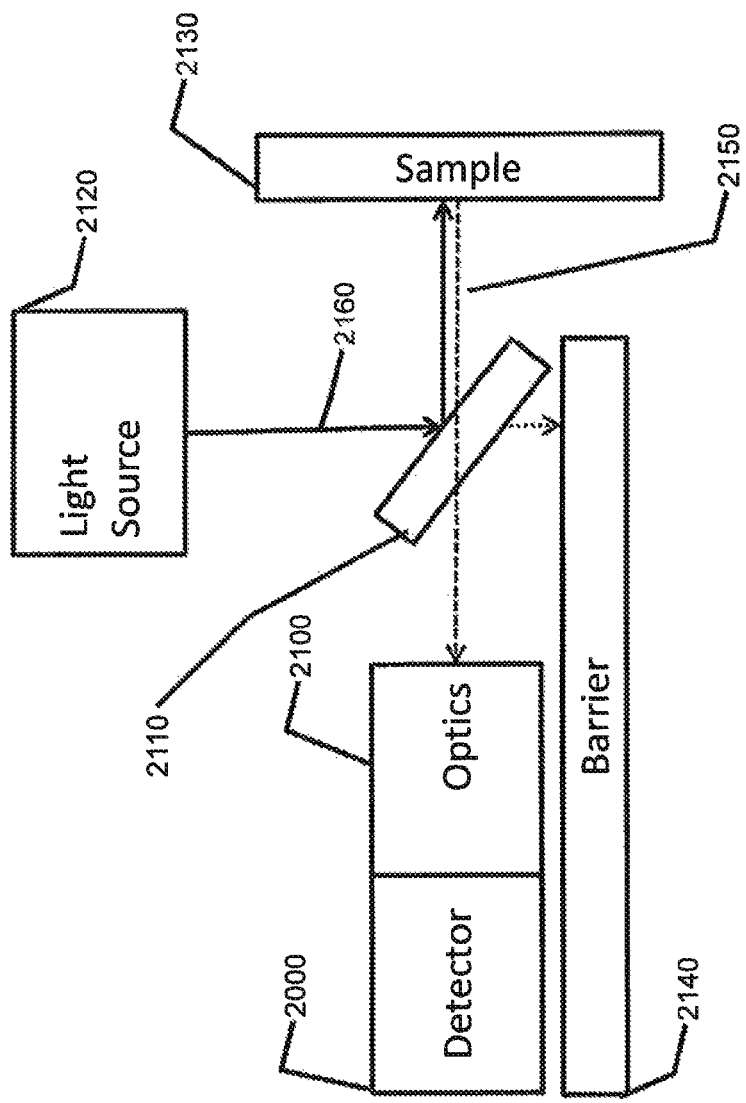

LATENT FINGERPRINT DETECTORS AND FINGERPRINT SCANNERS THEREFROM

CROSS REFERENCE TO RELATED APPLICATIONS

This is a Divisional of U.S. application Ser. No. 13/976,177 filed Jul. 29, 2013, which is a U.S. national phase of International Application No. PCT/US2011/059008 filed Nov. 2, 2011, which is a Continuation of U.S. application Ser. No. 13/049,351 filed Mar. 16, 2011, now U.S. Pat. No. 8,437,517 issued May 7, 2013, which claims the benefit of U.S. Provisional Application No. 61/409,753 filed Nov. 3, 2010, and incorporated herein by reference in their entirety.

U.S. GOVERNMENT RIGHTS

The U.S. Government has certain rights to disclosed embodiments based on Contract No. W911NF-10-C-0029 between Lockheed Martin Corporation and the U.S. Army.

FIELD

Disclosed embodiments relate to non-contact automatic optical detection of latent fingerprints.

BACKGROUND

Latent prints are invisible fingerprint impressions left on solid surfaces following surface contact caused by the perspiration on the ridges of an individual's skin on their fingers coming in contact with a surface and leaving perspiration behind, making an impression on it. Such fingerprint impressions may include substances like water, salt, amino acids, oils and also grime and various substances a person may have on their fingertip(s) or that may be present on a surface and able to accept an impression.

Conventional methods for extracting fingerprints usually involve adding chemicals or powders to the print. Such conventional methods can present an immediate dilemma in that they force the investigator to make a decision as to whether to dust for prints versus swabbing for DNA or chemical evidence present in the makeup of the print. Furthermore, such conventional methods are time-consuming and inconsistent, requiring some amount of trial-and-error on the part of an investigator before finding a technique suitable for a particular fingerprint composition and fingerprint-bearing surface combination.

Automatic non-contact latent fingerprint detection systems are also known that avoid the need to add chemicals or powders that can disturb the surface chemicals of the fingerprint. Such systems generally include a single light source, utilize only diffuse reflectance (and are, like most imaging systems, specifically configured to reject specular reflection (glare)), and are generally limited to fingerprinting the area of one's finger, or an area about that size.

SUMMARY

Disclosed embodiments include non-contact automatic optical fingerprint systems that include a critically aligned optical sensor comprising a light source positioned relative to a camera to utilize specular reflection from an irradiated sample surface. In contrast, conventional optical fingerprint systems reject specular reflection (glare) and process only diffuse reflection. It has been discovered that fingerprint features can be seen in images enabled by processing glare that cannot be seen in images generated using conventional diffuse reflected light. When the optical sensor is critically aligned and the camera exposure time and gain settings are set so that the specular reflections received do not saturate the camera's photosensor array, the diffuse reflections from interrogated sample surfaces will appear (relatively) very dim. In this arrangement, the diffuse reflections may not be visible at all.

Glare is usually most pronounced from a surface at those locations where the angles of incidence reflection are equal. At the critical alignment angle, the angles of incidence and reflection are substantially equal so that the specular reflection is directed mainly at an optical detection device (such as a camera). "substantially equal" refers to the angles being within 10%, and typically within 5%, of each-other.

The critically aligned optical sensor and camera settings can therefore act as a filter discriminating highly against diffuse reflections from scattering surfaces therefore providing a "geometric filter" that essentially only accepts glare (i.e., at least 90%, and more preferably at least 98%, of the photons processed by the camera are from the glare).

Discrimination for glare can be further enhanced when the numerical aperture (NA) of a lens or optical system associated with the optical detection device is set to zero. As known in optics, the NA of an optical system is a dimensionless number that characterizes the range of angles over which an optical system can accept light (for a light collector, e.g., camera) or emit light (for a light source). A numerical aperture of zero means that the optical system is configured to accept only directly incoming light, further reducing the effect of diffuse reflection.

Disclosed embodiments also recognize that having the light source and the optical system configured with equal and opposite NAs that are critical angle aligned together provides even more highly discriminating results for glare. Although a solution where the NA of the lens and the NA of the camera are both zero meets the requirements of equal and opposite NAs, this is only one solution of many that meet this condition.

As used herein, the light source and the optical system having "substantially equal and opposite. NAs" refers to the respective NAs being within 10%, and typically within 5%, of a magnitude of one another, and being opposite in sign. Disclosed fingerprint systems comprise a critically aligned optical sensor that includes a first light source for interrogating a sample surface within a region of interest with a collimated beam that can provide collimated photons that uniformly extend over the sample surface. As used herein, "uniformly extended" refers to an irradiated intensity of the collimated beam that varies ≤±20% across the area of the sample surface. The optical system may one or more lenses and be coupled to a photodetector array. The optical system and detector combination may have field of view (FOV), wherein the FOV is sufficiently large to image at least substantially an entire area of the sample surface.

A computer or processor having associated memory that includes reference fingerprint templates may be configured to receive a digitized form of the image data from the photodetector. The computer or processor may include data processing software for (i) comparing the digitized form of the image data to reference fingerprint templates to determine whether the image data includes at least one fingerprint, and (ii) for generating a fingerprint image if a fingerprint is determined to be present.

Automatic fingerprint scanning systems are also disclosed. Disclosed automatic fingerprint scanning systems comprise a disclosed automatic optical fingerprint system together with a scanner mechanically coupled to the optical sensor for scanning the optical sensor across a plurality of different surface portions within the region of interest, and optionally also a wireless transmitter for transmitting data representing fingerprints detected by the system to at least one remote site.

Variations of the systems and methods discussed herein may pertain to a latent fingerprint detection system, comprising: a first light source that illuminates a sample surface such that the sample surface produces specular reflection; and an optical detector arranged at a critical alignment angle relative to the first light source such that the optical detector captures the specular reflection from the sample surface and generates image data using essentially only the specular reflection to generate image data of the sample surface; and an image processor that analyzes said generated image data to determine if said generated image data includes a fingerprint; and produces image data of the fingerprint responsive to a determination that said analyzed image data includes a fingerprint.

In some variations, the first light source and said optical detector have substantially equal and opposite numerical apertures.

In some variations, the optical detector is aligned relative to said sample surface at an alignment angle that is substantially equal to an angle of reflection from the sample surface of the light provided by said first light source.

In some variations, the first light source comprises a broadband light source. In further variations, the first light source provides a collimated beam of light. In yet further variations, the collimated beam comprises a narrowband beam. In other variations, the light source comprises a narrowband light source including an ultraviolet (UV) wavelength. In yet other variations, the first light source comprises: a broadband light source; and a spectral filter in optical communication with the broadband light source. In yet other variations, the first light source is a laser operating at a wavelength of less than 600 nm. Still other variations, the collimated beam is an infra-red (IR) beam including at least one of a wavelength at 3.42 μm, 5.71 μm, 6.9 μm, or 8.8 μm.

In some variations, the image processor analyzes said image data of the sample surface to determine if said image data includes a fingerprint by performing slope detection. In other variations, the system further comprises a second light source that illuminates a sample surface such that the sample surface produces diffuse reflection. In yet other variations, the system further comprises: at least one scanner mechanically coupled to said optical detector for scanning said optical detector across a plurality of regions of interest on said sample surface.

In some variations, the first light source is a plurality of parallel aligned fluorescent tubes arranged to collimated light as well as non-collimated light. In other variations, the optical detector includes an optical arrangement that directs and focuses incoming light onto a detector portion, and where a numerical aperture of said optical arrangement is zero.

In some variations, the system flintier comprises: a second light source that illuminates the sample surface such that the sample surface produces specular reflection; and a third light source that illuminates the sample surface such that the sample surface produces specular reflection; where the sample surface is thermal printer dye film; and where a wavelength band of at least one light source substantially matches an absorption spectrum of said dye film. In other variations, the sample surface is glossy paper.

Variations of the systems and methods discussed herein may pertain to a method of detecting surface contaminants using specular reflection, comprising: illuminating a sample surface with a first light source such that the sample surface produces specular reflection; arranging an optical detector at a critical alignment angle relative to the first light source such that the optical detector captures the specular reflection from the sample surface and generates image data using essentially only the specular reflection to generate image data of the sample surface; analyzing said generated image data of the sample surface to determine if said generated image data includes an image of a surface contaminant; and producing image data of the contaminated area responsive to a determination that said analyzed image data includes an image of a surface contaminant.

In some variations, arranging includes configuring said first light source and said optical detector such that they have substantially equal and opposite numerical apertures. In other variations, arranging includes aligning said optical detector relative to said sample surface at an alignment angle that is substantially equal to an angle of reflection from the sample surface of the light provided by said first light source.

In some variations, illuminating includes providing a collimated beam of light. In further variations, providing a collimated beam of light includes providing a narrowband beam. In other variations, illuminating includes providing narrowband light in an ultraviolet (UV) wavelength. In yet other variations, illuminating includes providing broadband light; and spectrally filtering said broadband light such that said sample surface is illuminated with spectrally filtered light. In still other variations, illuminating includes illuminating the sample surface with a laser operating at a wavelength of less than 600 nm. In yet other variations, illuminating includes illuminating the sample surface with an infra-red (IR) beam including at least one of a wavelength at 3.42 μm, 5.71 μm, 6.9 μm, or 8.8 μm.

In some variations, the surface contaminant is a fingerprint and said analyzing includes performing slope detection on said image data of the sample surface. In other variations, the method further comprises second illuminating a sample surface with a second light source such that the sample surface produces diffuse reflection. In yet other variations, the surface contaminant is a fracture or physical defect in the sample surface.

In some variations, illuminating a sample surface with a first light source further comprises illuminating said sample surface with a plurality of parallel aligned fluorescent tubes arranged to collimated light as well as non-collimated light. In other variations, arranging further includes setting a numerical aperture of said optical detector to zero.

Variations of the systems and methods discussed herein may pertain to a method of detecting latent fingerprints using specular reflection, comprising: first arranging a first light source such that it illuminates a sample surface so that the sample surface produces specular reflection; and second arranging an optical detector at a critical alignment angle relative to the first light source such that the optical detector captures the specular reflection from the sample surface and generates image data using essentially only the specular reflection to generate image data of the sample surface; analyzing said generated image data of the sample surface to determine if said generated image data includes an image of a fingerprint; and producing image data of the fingerprint responsive to a determination that said analyzed image data includes an image of a fingerprint.

Variations of the systems and methods discussed herein may pertain to a latent fingerprint detection system, comprising: a light source alignment portion configured to align a light source at an illumination angle relative to a sample surface such that said light source illuminates said sample surface so that the sample surface produces specular reflection; and a specular reflection discriminator configured to direct the produced specular reflection to optical detector aligned relative to said sample surface at an alignment angle that is substantially equal to an angle of reflection of the produced specular reflection such that the directed specular reflection does not saturate the optical detector; and the optical detector captures the specular reflection from the sample surface and generates image data using essentially only the specular reflection to generate image data of the sample surface.

In some variations, the system further comprises an image processor that: analyzes said image data of the sample surface to determine if said image data includes a fingerprint; and generates image data of the fingerprint responsive to a determination that said analyzed image data includes a fingerprint. In further variations, the image processor analyzes said image data of the sample surface to determine if said image data includes a fingerprint by performing slope detection.

In some variations, the system further comprises: at least one seamier mechanically coupled to said optical detector for scanning said optical detector across a plurality of regions of interest on said sample surface, where said scanner is configured to maintain the critical alignment angle during scanning.

In some variations, the discriminator includes an optical arrangement coupled to the optical detector and where the optical arrangement has a numerical aperture of zero. In other variations, the numerical apertures of the light source and the optical detector are substantially equal and opposite. In yet other variations, the specular reflection discriminator includes a partial reflector that is arranged to: direct a portion of illumination from said light source towards the sample surface in a direction perpendicular to the sample surface; and direct a portion of specular reflection from the sample surface into the optical detector, which is arranged to detect light coming in a perpendicular direction from the sample surface.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 1D is a depiction of a fingerprint detection system as described herein;

FIG. 1E is a depiction of a glare-based imaging system as described herein;

Figure 1A:
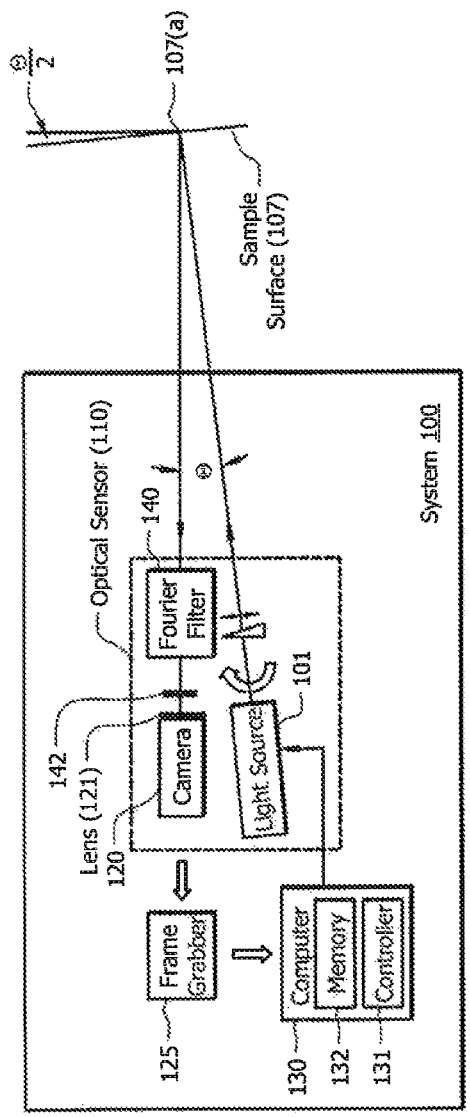
FIG. 1A is a depiction of a fingerprint detection system as described herein.

The drawings will be discussed further in the detailed description.

DETAILED DESCRIPTION

Disclosed embodiments are described with reference to the attached figures, wherein like reference numerals, are used throughout the figures to designate similar or equivalent elements. The figures are not drawn to scale and they are provided merely to illustrate aspects disclosed herein. Several disclosed aspects are described below with reference to example applications for illustration. It should be understood that numerous specific details, relationships, and methods are set forth to provide a full understanding of the embodiments disclosed herein. One having ordinary skill in the relevant art, however, will readily recognize that the disclosed embodiments can be practiced without one or more of the specific details or with other methods. In other instances, well-known structures or operations are not shown in detail to avoid obscuring aspects disclosed herein. Disclosed embodiments are not limited by the illustrated ordering of acts or events, as some acts may occur in different orders and/or concurrently with other acts or events. Furthermore, not all illustrated acts or events are required to implement a methodology in accordance with this Disclosure.

When illuminating a surface to collect image data thereof, the surface may reflect the illumination in one of two principal ways: specular reflection (glare) and diffuse reflection. Generally, optical imaging systems work to collect image data based on diffuse reflection and eliminate or minimize the image component associated with specular reflection. The systems and techniques of this disclosure, by contrast, utilize the specular reflection component as at least part of the image data used to create an image of a surface reflection.

Glare is usually most pronounced from a surface at those locations where the angles of incidence reflection are equal. Most surfaces exhibit both diffuse and specular reflection properties, but most imaging systems favor diffuse reflection and exclude, reject, or produce unusable results from specular reflection. Especially as it relates to the realm of fingerprint imaging, specular reflection.

An embodiment of a fingerprint imaging system is depicted in FIG. 1D. The system includes a light source 1110, which may or may not be filtered 1120 depending on the illumination requirements. Variations of a light source may include narrow band or broad spectrum light sources in visible, IR, or UV spectra or combinations thereof. Variations of a filter may include band-pass filters, notch filters, spectrometers, prisms, waveband-specific mirrors, filter coatings, and other devices, materials, and techniques for filtering electro-optical radiation produce one or more specific illumination wavelength ranges. The resulting illumination may be a collimated, narrow beam directed at a sample 1130 surface. Preferably, the illumination is collimated and narrow to provide increased specular reflection from the sample surface to the detector 1100. Specular reflection (glare) may be pronounced in situations where an angle of incidence and angle of reflection are the same. Some variations may therefore align the light source 1110 and detector 1100 at a critical alignment angle to facilitate the creation and capture of specular reflection from the illuminated surface 1130. This critical alignment angle is one where the angle of incidence and angle of reflection for are equal relative to the illuminated surface 1130. This is the angle at which specular reflection is most pronounced.

By maintaining this critical alignment between the light source(s) 1110 and the detector 1100, the light source and image detector may be configured to behave as a filter that discriminates against diffuse reflections and essentially only accepts specular reflection (glare) as input into the image detection device. In some variations, the detector settings may be further configured to create a "geometric filtering" effect that causes over 90% of the photons processed by the camera to be from the glare. Such configuration may be realized by setting a numerical aperture of a lens or optical arrangement (not shown) coupled to the detector 1100 to be zero. Such configuration may also be realized by setting the numerical apertures of the optical arrangement and the light source to be substantially equal and opposite.

In some variations, the detector 1100 and light source 1110 may be aligned and configured so that the detector essentially only uses photons from glare. In this case, the term "essentially only" means that at least 90% and more preferably at least 98% of the photons processed by the detector 1100 are from the glare.

In some variations, the detector 1100 may be coupled with or part of an image processor 1001. Some variations may use a CCD or CMOS camera device which has image detection and image processing capabilities. Preferably, the image processor 1001 is configured or otherwise designed to extract image data from specular reflection. In some variations, a customized or purpose-built or purpose-programmed image processor may be required. In some variations, the light source 1110 may be designed, configured, or otherwise controlled to provide illumination that approaches a saturation threshold of the detector 1100. Preferably, the light source does not reach the saturation threshold of the detector in order to avoid loss of contrast or other loss of image data due to detector saturation.

FIG. 1E depicts an embodiment of a glare-based surface imaging system which may be used for fingerprint detection applications. The system includes a light source 2120 and optical detector 2000 arranged in concert with one or more specular reflection discrimination components intended to produce and direct non-saturating specular reflection 2150 into the optical detector 2000 for image generation.

In the variation shown, a partial reflector 2110 is used to direct a portion of light 2160 from the light source directly onto (i.e. in a direction perpendicular to) a sample surface 2130. Because the angle of incidence and angle of reflection for specular reflection are equal, the glare 2150 produced from the sample surface 2130 will be directed, in the embodiment shown, in a perpendicular direction away from the sample surface 2130. The detector 2000 may be arranged along the path of the specular reflection 2150, which passes through the partial reflector 2110 (either completely or partially, depending on the type of partial reflector used) and enters the detector 2000 where it is used to produce image data.

In some variations, the detector may be equipped with or combined with an optical arrangement 2100 to further enhance the collection of glare 2150. In some variations, the numerical aperture of the optics (which may include one or more lenses or lens arrangements) may be set to zero, such that the optics discriminate highly against anything but directly incoming 2150 light. In other variations, the light source 2120 and optics 2100 may both be configured with substantially equal and opposite numerical apertures. In such variations, a partial reflector 2110 or other illumination redirecting component may be omitted, with the sample surface being directly illuminated.

In some variations, for further improvements in performance, one or more light barriers 2140 may be disposed around the detector 2000 or sample surface in order to absorb diffuse reflection and thereby reduce the amount of diffuse reflection entering the detector 2000.

FIG. 1A also depicts an embodiment of a fingerprint imaging system 100. In the embodiment shown, an optical sensor 110 arrangement includes an image detection device 120 such as a camera or a focal plane array. In some variations, the image detection device 120 may include or be coupled with a lens 121 to focus incoming electro-optical radiation. In variations where the detector 120 is a camera that is positioned at the critical alignment angle in conjunction with a light source 101, further improvements in collection of glare photons and rejection of diffusely reflected photons may be realized by configuring the numerical apertures of the camera 120 and the light source 101 such that they are of equal and opposite value.

In the variation shown, a light source 101 is also included in the optical sensor 110. Such a variation may be realized as, for instance, a light source and a camera arranged in a single housing or similar alignment tool or mounting device that establishes or maintains a critical alignment angle between the detector 120 and the light source 101. In other variations, the light source 101 may be physically separate from the optical sensor 110 and may be controlled or otherwise configured to provide specific illumination based on imaging parameters or requirements. Such specific illumination may include varying degrees of collimation and angle-of-incidence from the light source 101 relative to an area of interest 107(*a*) on a sample surface 107 that is to be imaged.

Variations of a fingerprint imaging system may also include or be connected to a computer or processor 130 that processes the image data acquired by the image detection device 120. Such a computer or processor 130 may, in some variations, be equipped with a memory 132 for storing data and a controller 131 for controlling some or all of the optical sensor portions or related components thereof. In some variations, the light source 101 may be configured or controlled to provide a uniformly extended, collimated beam onto the sample surface 107

In some variations, the collimated beam provided by light source 101 may have a spatial extent greater than the field of view of the image detection device 102 (or, in lens-equipped variations, than that of the lens 121). In one embodiment the area of interest 107(*a*) illuminated by the collimated beam is 50 μm×50 μm and the field of view of the image detection device 102 is less than 50 μm×50 μm.

Figure 1B:
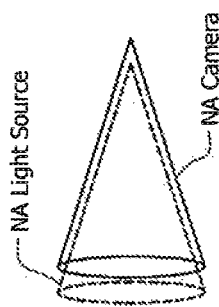
FIG. 1B illustrates a depiction of NA matching along with NA alignment between a light source and a detector.

As depicted in FIG. 1B, the light source 101 and the image detection device 120 may also have substantially equal and opposite numerical apertures (NAs). In some variations, these NAs are aligned together to favor the creation and detection of specular reflection at the sample surface 107. One method for NA alignment is configure the image detection device 120 and light source using a sample having known or predetermined properties and one or more neutral density optical filters. Adjustment can be made using bright light until the best response is obtained. A filter can be added to dim the illuminating light and the best performance can be obtained again. Another filter can then be added, etc. For instance, if the two NAs are conically shaped and opposite in sign they can be stacked almost perfectly one on top of the other as shown in FIG. 1B.

Optically aligning the light source 101 and image detection device 102 NAs, and configuring the light source 101 to provide a uniformly extended collimated beam over the sample surface 107 creates a uniform glare field across the field of view of the image detection device 102. In some variations, a uniform glare field can maximize the dynamic range of the imaging system. In such variations, non-uniformities in the illumination field serve as a noise floor. A wide dynamic range with good SNR provides high contrast for better image acquisition.

Some variations of a light source 101 can comprise a broadband light source. For example, the broadband light source can comprise a fluorescent light source, such as a plurality of parallel aligned (i.e., stacked) fluorescent tubes. In some variation of aligned fluorescent tubes, an alignment of fluorescent bulbs can create a light source that emits collimated light as well as non-collimated light. In some variations, the collimated light has a NA=0 and using a camera lens with NA=0 causes the camera to be very sensitive to the collimated light. Using a variation of a light source created from stacked fluorescent tubes and aligned at a critical alignment angle with the image detection device 102 may, in some variations, effectively cause the detection device 102 to disregard or otherwise show significantly reduced sensitivity to the non-collimated light.

In another embodiment the collimated beam provided by light source 101 comprises a narrowband beam defined herein as <1 nm Full Width Half Max (FWHM). Other variations may include narrow-band light source(s) in the visible, UV, or IR spectra (or combinations thereof) or broad-band light source(s) that emit across one or more of the UV, visible, and IR spectra. Such broad-band light source(s) may be coupled with one or more filters to tailor the illumination spectrum at the sample surface to a particular wavelength or range or set of wavelengths.

A narrowband beam can be realized by a narrowband light source (e.g., a laser, a UV lamp, other narrow-spectrum illumination source), or a broadband light source (such as a flash lamp, a fluorescent light, or a broad-spectrum LED) and a spectral or waveband filtering device such as a band-pass filter or a spectrometer. In some embodiments, the light source may be selected, filtered, or otherwise configured such that the sample surface 107 may be illuminated at one or more UV wavelengths or one or more LWIR wavelengths that correspond known absorption spectra for fingerprint oil(s). Such wavelengths, in some variations, may be defined as wavelengths where absorption for compounds associated with fingerprints increases by at least 6.5% as compared to the absorption in a conventional range from visible light range to 3 μm. Increased absorption has been found to provide improved contrast by making the fingerprint stand out against the sample surface (which provides the background in the image—See FIG. 4) Certain UV and IR wavelengths provide significantly enhanced absorption. In one embodiment the UV wavelength is between 100 and 300 nm, and the LWIR wavelength can be at 3.42 μm, 5.71 μm, 6.9 μm, or 8.8 μm, which all represent enhanced absorption wavelengths for fingerprint oil.

Variations of a light source 101 can provide either non-polarized or polarized light. Polarized light may be of advantage in variations where the sample surface 107 is held at an extreme angle, something analogous to Brewster's angle (polarization angle). This angle is defined by the surface material and surface roughness/texture. Certain otherwise transparent or translucent materials may provide improved specular reflection when illuminated with polarized light under such conditions.

Variations of the image detection device 120 (and, in lens-bearing embodiments, associated lens 121) may include a variety of different camera types, such as commercial off-the shelf (COTS) CCD/CMOS digital cameras, infra-red (IR) cameras, ultra-violet (UV) cameras, millimeter-wave detectors, and other camera types. Any required or associated lens magnification, camera sensor size, and pixel count can be selected or designed to produce a minimum resolution that is compatible with existing requirements. For example, 500 DPI is the current FBI standard.

In one embodiment, the image detection device 120 is sensitive to radiation including UV radiation in the range from about 100 nm to 300 nm. This UV imaging capability can be provided by using a UV camera or by using a UV sensitizer material in combination with a visible-spectrum detection device 120 such as a camera sensor. One UV sensitizer material has the commercial name Lumigen (Lumigen, Inc. (a Beckman Coulter Company; Southfield, Mich.). The UV sensitizer material may be applies as a layer that absorbs UV light and converts it to a wavelength that photodetectors such as CCD photodetectors can efficiently detect.

In one embodiment the lens 121 is selected to provide $NA_{Camera}=0$. For example, a double telecentric lens can provide $NA_{Camera}=0$ which results in the $FOV_{Camera}=$area of the lens 121. The image detection device 120 may include or be coupled to a computer or processor 130. In some variations, this coupling may be accomplished via a frame grabber 125. A frame grabber 125 is an electronic device that captures individual, digital still frames from an analog video signal or a digital video stream. In some variations, a frame grabber 125 may be omitted or may be integrated either into the computer 130 or image detection device 120. Some variations of cameras may have integrated or otherwise built-in frame grabbers or frame grabber capability.

Other embodiments may use different numerical aperture settings. Preferably, the numerical aperture of the camera and the numerical aperture of a glare-producing light source will have equal and opposite values to enhance and improve both the creation and detection of glare.

Variations of a computer or processor 130 include a controller 131 that can dynamically control the intensity of light provided by light source 101, and at least one memory 132. The intensity of light source 101 can be set to approach saturation of the image detection device 120. In some variations, light source intensity may be set to ensure that it does not actually reach saturation levels of the image detection device 120.

The standoff distance during imaging operations is generally set by the resolution and focal length of the image detection device 120 (which may or may not include the lens 121). In some variations, the standoff distance between the optical sensor 110 and sample surface 107 may be about 12 inches. Other variations may employ standoff distances of as little as 4 inches or less, or 20 inches or more. Variations using highly collimated, intense light sources or laser illumination sources may employ stand-off distances of several feet or more.

Light source 101 can be dynamically adjusted to maintain critical alignment angle shown with respect to the image detection device 120. In some variations, such adjustment may be accomplished with movable mirrors, refractive devices, prisms, or combinations thereof. In one embodiment both the light source 101 and the image detection device 120 are secured to a fixture to maintain critical alignment angle even when the entire system 100 is moved.

Some variations of the system 100 may include at least one detection filter, shown such as a Fourier filter 140 or a notch filter 142. Some variations may be equipped with multiple detection filters, other variations may have no detection filters or may have detection filters integrated into a image detection device 102. Variations of a notch filter 142 may included for embodiments using a laser (not shown) for critical alignment purposes or as a diffuse scatter light source. Variations of a Fourier filter 140 may be used to match fingerprint features as well as suppress background features, such as grains or surface irregularities in the variations performing detection on a paper or cardboard sample surface 107, such as for Raman imaging.

Disclosed embodiments recognize in order to detect fingerprints that may be on a wide variety of different surfaces, such as tools (e.g., wrenches), guns, phones/PDAs and CD cases, multiple different illumination wavelength bands or ranges may be desired. Each wavelength band can provide a different kind of light, such as white light, narrowband light, UV, IR, or other specific wavelengths, wavelength ranges, or wavelength combinations of electro-optical radiation. Such variation in wavelengths or wavelength ranges may be realized with one or more very broad spectrum light sources and a configurable filtering solution (such as adjustable filters, multiple filters that can be activated or de-activated, or refraction or reflection techniques that separate out only particular wavelengths, or combinations thereof) or with multiple individual light sources configured to produce one or more of the desired wavelengths or wavelength ranges.

In variations using multiple illumination wavelengths or wavelength ranges, light from each wavelength range may scatter off an interrogated sample surface 107 differently. The wavelength ranges may be used one at a time, with each range producing a different effect on the latent fingerprint, or, in some variations, multiple wavelength ranges may be combined simultaneously during illumination.

Figure 1C:
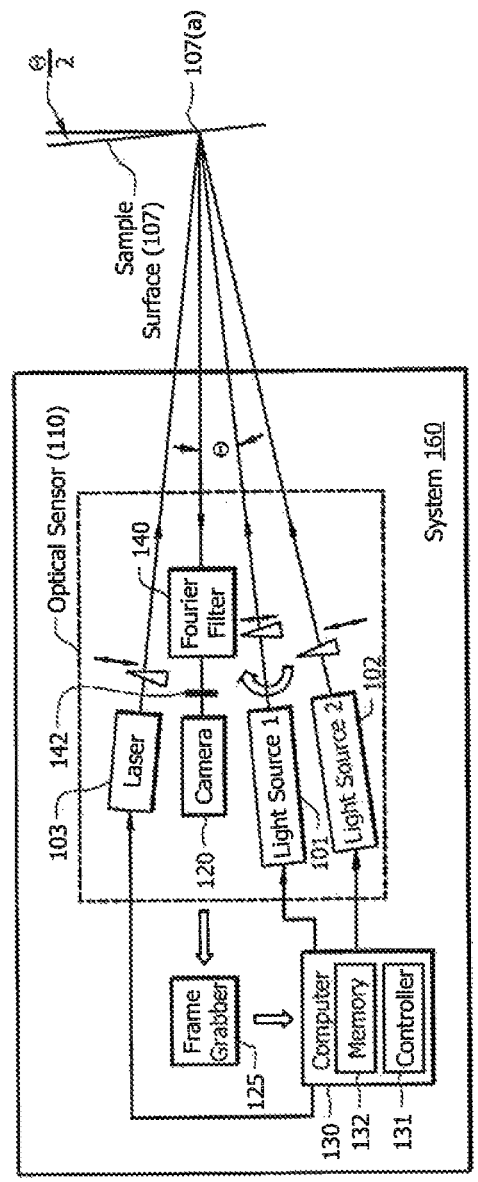
FIG. 1C is a depiction of a fingerprint detection system as described herein.

FIG. 1C is a depiction of an example fingerprint system 160 comprising a an optical sensor including a image detection device and a light source 101, where the light source 101 provides a uniformly extended collimated beam for interrogating sample surfaces including a first sample surface within a region of interest. The system 160 also includes additional light sources 102 and 103. Diffuse scatter from the additional light sources 102 and 103 allows the background to be characterized so that the background can be subtracted out from the image data, such as text on paper in the case of certain paper-based samples. In some variations, the light source 101 is critically aligned to generate a high level of specular reflection whereas the additional light sources 102, 103 are not critically aligned.

Variations of a system 160 may also include a computer or processor 130 for data processing the glare and diffuse refection data received by the image detection device 120. In one embodiment, one additional light source 102 may provide incandescent light, and another additional light source 103 may be a laser. Light sources 101-103 each can include dynamic intensity adjustment. In some variations, the respective light sources 101-103 may individually illuminate the sample surface 107 for separate interrogations.

Light from a laser, for instance, can reveal latent fingerprints that other light sources. In some variations, a laser may be used to excite the sample surface in a very specific (narrow) spectral band and time domain, such as at 532 nm. Spectral/temporal filtering methods can be used to extract the desired information from such laser illumination of the sample surface. The type of image detection device used to record the results may vary based on the type of optical filtering employed to extract the data. For instance, if Raman imaging is used in conjunction with a camera, the camera exposure time will be approximately the same value as the length of the laser pulse. This technique can reduce background noise due to fluorescence.

In some variations, a multiple light-source variation may be used for imaging specialized substrates or surfaces, such as thermal dye printer film. For variations meant to scan thermal dye printer film using CMY color panels (Cyan, Magenta, and Yellow), three narrow-band light sources at or near the absorption wavelengths for the respective color panels may be used. In such variations, wavelength-dependent image contrast techniques may be utilized. Additionally, as discussed above, by maintaining critical alignment angle between the light source(s) 101-103 and the image detection device 120, the light source and image detector may be configured to behave as a filter that discriminates against diffuse reflections and essentially only accepts specular reflection (glare) as input into the image detection device. The combination of wavelength-dependent image contrast and critical alignment angle allows for the detection of any previously printed images on the thermal dye film as well as any latent fingerprints that may be present on the dye film.

Figure 2:
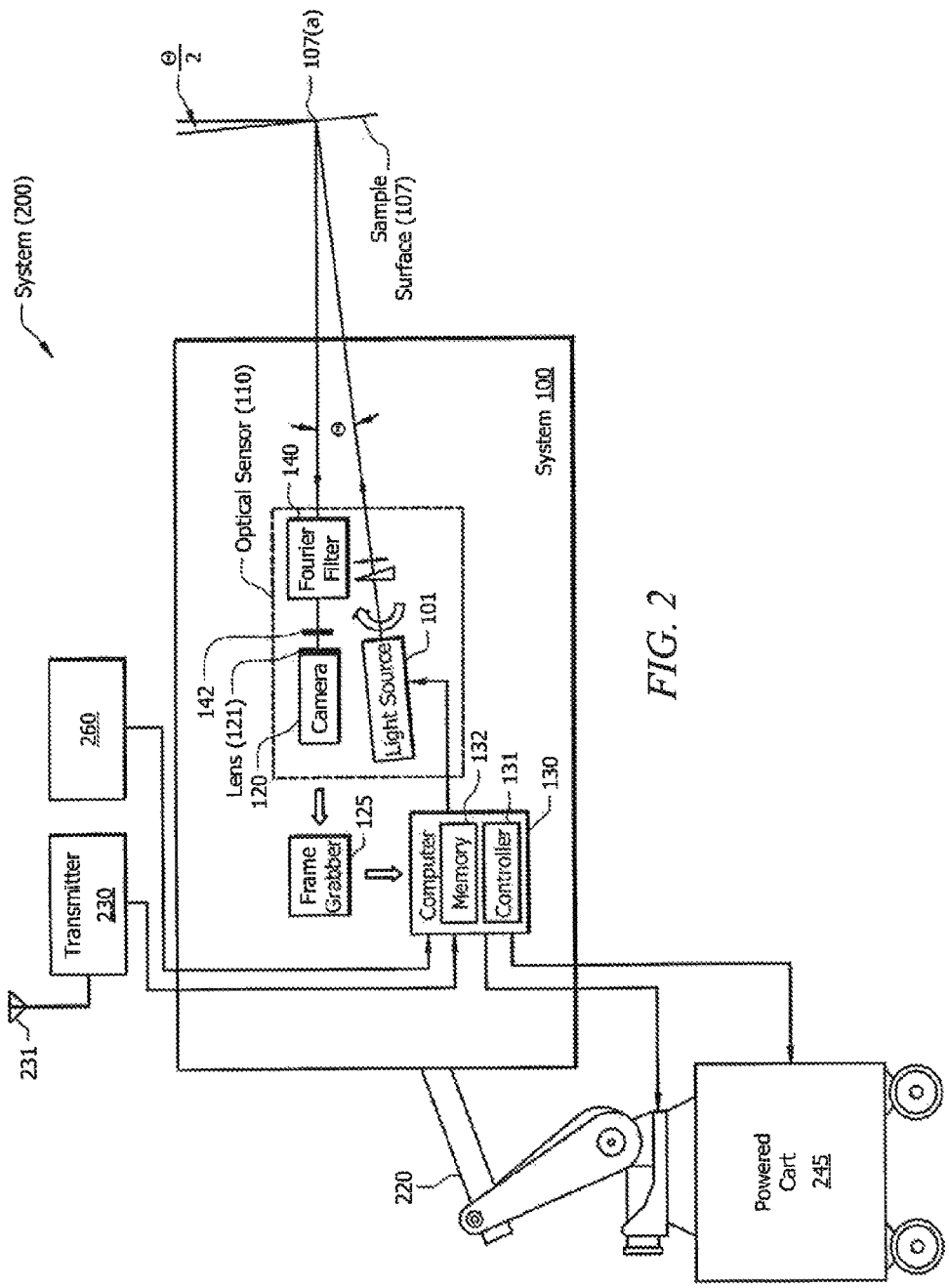
FIG. 2 is a depiction of a fingerprint detection system as described herein.

FIG. 2 is a depiction of an embodiments of an automatic fingerprint scanning system 200. In the embodiment shown, an embodiment of a fingerprint detection system 100 of the type discussed above may be combined with a scanner 220 shown as a robotic arm 220 mechanically coupled to the system 100 for scanning the optical sensor 110 across a plurality of different sample surfaces 107. Further variations may include a wireless transmitter 230 including an antenna 231 for transmitting data representing fingerprints detected by the system 100 to at least one remote site.

The embodiment shown may also be mounted on or connected to a powered cart 245, such as a battery powered cart. Robotic arm 220 may be affixed to the powered cart 245. Some variations of the system 200 may also include a remote sensing device 260 for generating a region image (e.g., 3D) across a region of interest, such as a room. The region image sensed by sensing device 260 is provided to computer or processor 130 and can be used to guide movements of the robot arm 220 for its movement to image across the region of interest, such as within a room.

In one variation of such a system 200, imaging results can be stored in a local memory 132 associated with the computer or processor 130, and can be wirelessly transmitted by a wireless transmitter 230, such as in an established encoded protocol form, to one or more remote locations. In one embodiment the remote sensing device 260 comprises a Light Detection And Ranging (LIDAR) device. LIDAR may also be referred to as LADAR in military contexts, and is an optical remote sensing technology that can measure the distance to, or other properties of a target by illuminating the target with light, often using pulses from a laser. Like the similar radar technology, which uses radio waves, the range to an object is determined by measuring the time delay between transmission of a pulse and detection of the reflected signal.

Figure 3A:
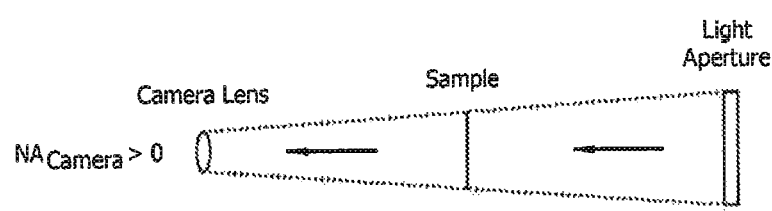
FIGS. 3A-C each depict arrangements of light source and camera NAs.
Figure 3B:
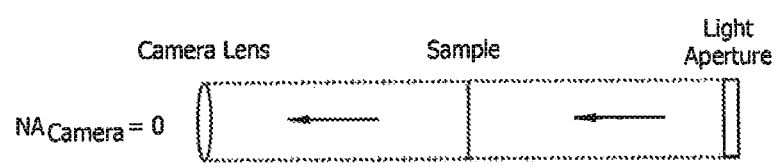
Figure 3C:
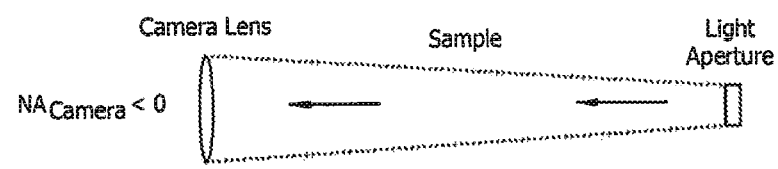

FIGS. 3A-C each depict different conditions shown unfolded around the sample axis that can satisfy the condition that the entire sample be uniformly illuminated using equal and opposite light source and $NA_{Camera}$, with the camera imaging the entire sample being irradiated, according to example embodiments. FIG. 3A shows the case of $NA_{Camera} > 0$. FIG. 38 shows the case of $NA_{Camera} = 0$. In this case the camera lens can be a double telecentric lens. An example of a light source that provides a zero NA is a highly collimated light source. FIG. 3C shows the case of $NA_{Camera} < 0$.

Figure 4:
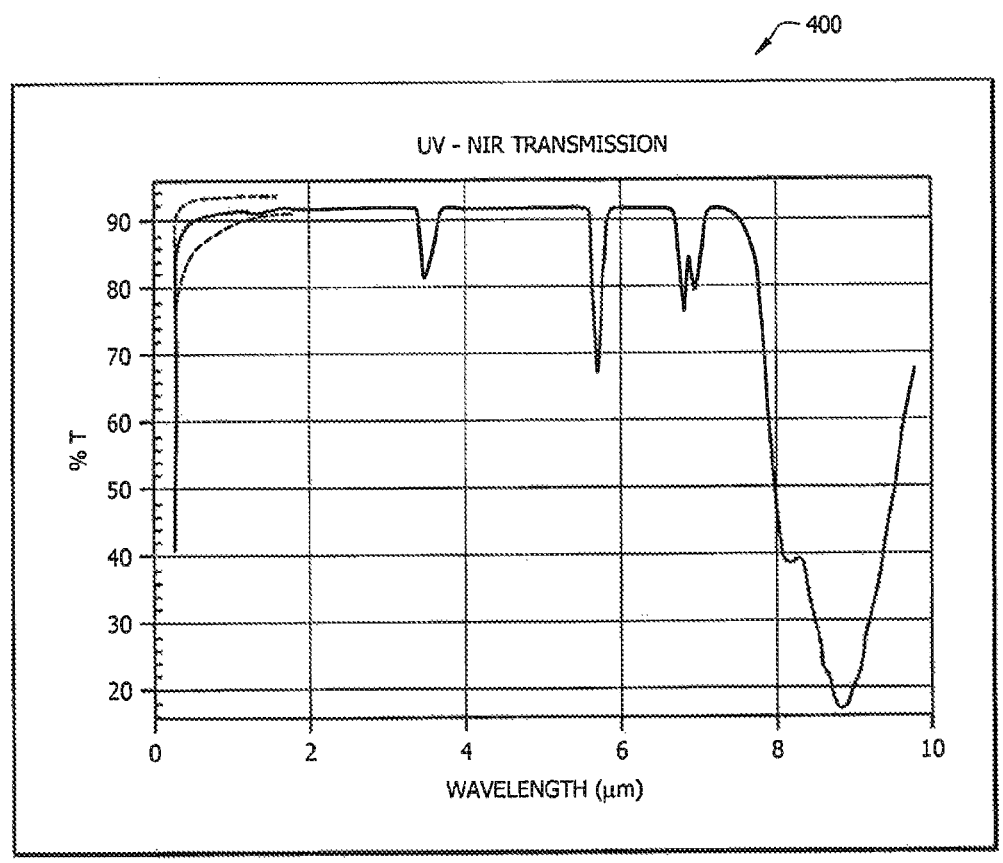
FIG. 4 is a plot transmission % from the UV to the Long Wave Infra-Red (LWIR) for fingerprint oil.

FIG. 4 is a plot 400 of UV to NIR transmission for fingerprint oil evidencing significantly enhanced absorption within the UV and the LWIR as compared to an absorption of fingerprint oil in a conventional visible light range (i.e. 500 nm) to 3 pin. The UV and LWIR can be used to image fingerprints exploiting heightened absorption to increase the optical contrast of the fingerprint oils against a sample surface, such as paper.

In the UV variation shown, 80% transmission is at about 300 nm (0.3 µm), with the transmission decreasing (and absorption increasing due to oil absorption) to about 40% at 180 nm, with even lower transmission down to below 100 nm (not shown). In the variation shown, enhanced absorption can thus be obtained at UV wavelength between 100 and 300 nm.

Several IR absorption peaks are shown. and LWIR wavelengths at 3.42 µm, 5.71 µm, 6.9 µm, and 8.8 µm. Other samples may have absorption peaks at different wavelengths in the IR. Operating at these peaks gives enhanced performance to a fingerprint detection system.

Figures 5A, 5B:
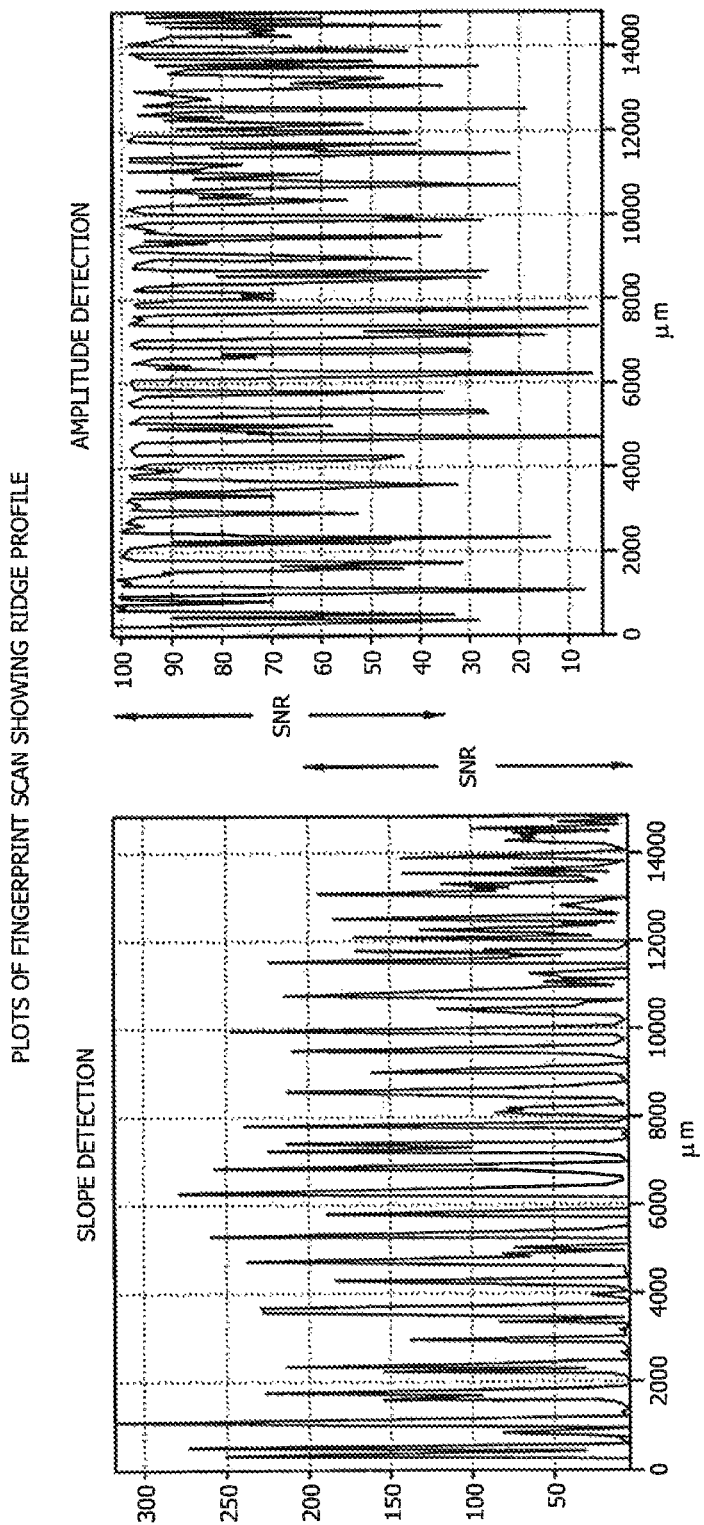
FIGS. 5A and B show signal to noise ratio (SNR) data from plots of fingerprint scans.

FIGS. 5A and 5B show signal to noise ratio (SNR) data from plots of fingerprint scans showing a ridge profile evidencing about a 3× improvement in SNR using slope detection (FIG. 5A) as compared to amplitude detection (FIG. 5B), according to an example embodiment. The best possible detection would be an idealized "Matched Detection" where an exact replica of the feature being sought is compared with the collected signal. Amplitude Detection looks only for an amplitude change, while slope detection looks for a part of the feature being detected.

Figure 5C:
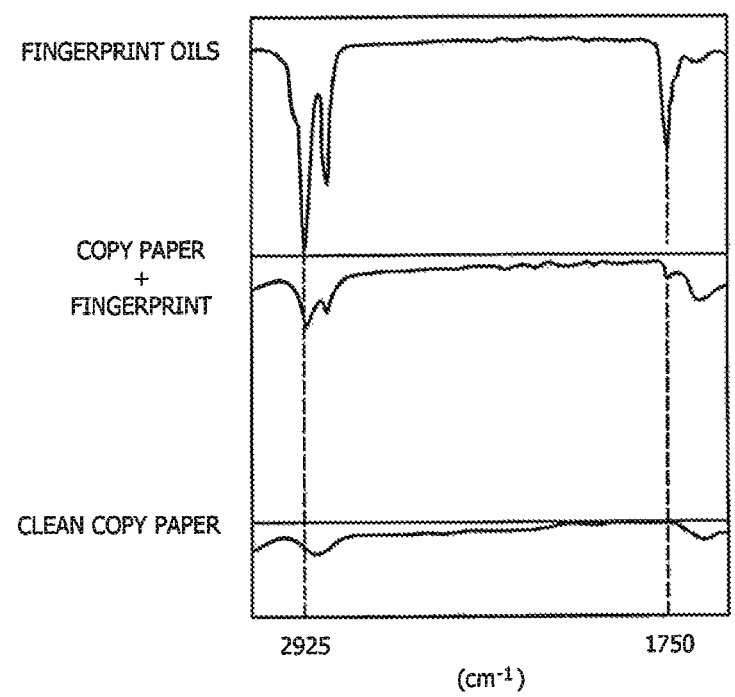
FIG. 5C shows spectral plots of the absorption for fingerprint oil.

FIG. 5C is provides spectral plots of the absorption for fingerprint oil, fingerprint oil on copy paper, and clean copy paper, showing an absorption peak at 3.418 µm (2925 cm$^{-1}$ which corresponds to a wavelength of 3.418 µm) that can be used to define sloped portions of this peak for slope detection, according to an example embodiment. In the case of slope detection the feature being detected can be the sharp slopes on each side of the peak at 2925 cm$^{-1}$.

Figure 6:
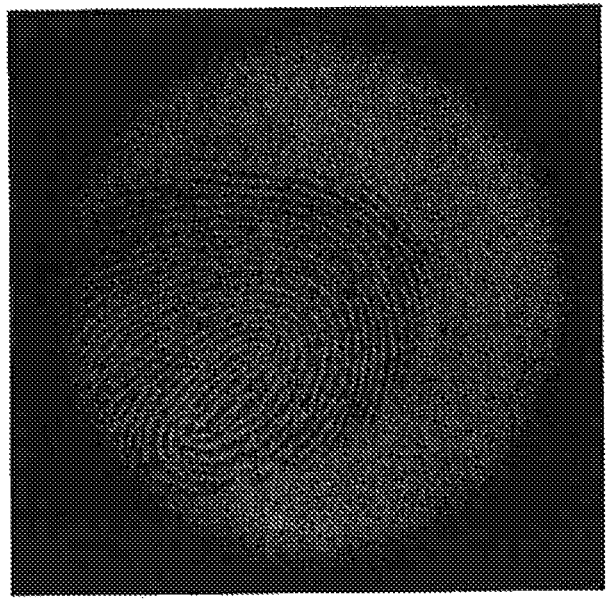
FIG. 6 is a scanned image of a fingerprint acquired by an example disclosed fingerprint system.

FIG. 6 is a scanned image of a fingerprint acquired by an example disclosed fingerprint system configured to be highly discriminating toward specular reflection from a sample surface including a critically aligned optical sensor having the light source and camera have equal and opposite NAs, according to an example embodiment. The camera used was a 6M Pixel CCD, the lens was a double telecentric lens, and the light source was a set of fluorescent light bulbs held side-by-side closely to each other in a parallel fashion. The light source, sample and camera plus lens were set up to satisfy the critical alignment angle condition.

Variations of disclosed systems, such as systems described above, may be configured to automatically generate fingerprint image data from sample surfaces within an interrogated region, and look for fingerprints in the fingerprint image data obtained. When a fingerprint is detected the system can capture the fingerprint, digitize it into a digital storage format (e.g., using an analog to digital converter), and can store it in memory, such as the internal memory 132 of computer 130. Computer 130 can comprise a laptop computer, personal digital assistants (PDAs), or other suitable portable computing device. Software on the portable computing device can then encode the stored fingerprints into a format usable by the existing AFIS (automated fingerprint identification system), integrated AFIS (JARS) or other fingerprint processing systems. In one application, disclosed systems can be used to help investigators locate latent fingerprints at a crime scene.

In one embodiment an internal matching algorithm helps the investigator(s) differentiate fingerprints of interest from those expected to see at the scene such as family members, co-workers, etc. Data from expected fingerprints can be loaded into the system and stored as reference fingerprint templates in local memory 132. Having the ability to immediately organize prints into classification groups can significantly benefit the investigators, helping them better focus their efforts.

Being automatic and computer controlled, disclosed embodiments reduce operator workload and minimize the potential for human error. Disclosed embodiments can also give the field investigator(s) the ability to immediately know that the data he/she gathers is valid and usable. Human error includes overlooking or possibly damaging critical evidence as well as incorrectly capturing fingerprint evidence. As described above, fingerprint data can be wireless transmitted to one or more remote locations using a wireless transmitter.

Disclosed fingerprint systems can be built into other systems to add security features to such systems, such as to reduce theft or unauthorized access. For example, credit or debit card processing systems can include disclosed fingerprint systems to provide a fingerprint record associated with each transaction that is triggered upon insertion of the card. Such fingerprint records can be used to identify the individual using the card, and if a fingerprint database is available, a fingerprint database can be used to determine whether account access will be provided.

Although disclosed in the context of fingerprint detection, the techniques and solutions discussed herein may be applied to the detection and identification of surface contaminants in general. The presence of a contaminant material on a surface may be a fingerprint, but may also be residue of cleaning solvents, lubricants, or particulate matter. The specular reflection imaging techniques discussed herein would be equally applicable for the detection of such contaminants as their reflection properties would be different from those of the surface being imaged due to either or both of material composition and surface texture. In high-precision manufacturing, for instance, cracks, burrs, and residues on a machined or polished surface may be identified using the techniques discussed herein. The variations in the glare field caused by surface texture and composition variations can be imaged and detected in a manner similar to the fingerprint detection techniques discussed above.

While various disclosed embodiments have been described above, it should be understood that they have been presented by way of example only, and not as a limitation. Numerous changes to the disclosed embodiments can be made in accordance with the Disclosure herein without departing from the spirit or scope of this Disclosure. Thus, the breadth and scope of this Disclosure should not be limited by any of the above-described embodiments. Rather, the scope of this Disclosure should be defined in accordance with the following claims and their equivalents.

Although disclosed embodiments have been illustrated and described with respect to one or more implementations, equivalent alterations and modifications will occur to others skilled in the art upon the reading and understanding of this specification and the annexed drawings. While a particular feature may have been disclosed with respect to only one of several implementations, such a feature may be combined with one or more other features of the other implementations as may be desired and advantageous for any given or particular application.

The terminology used herein is for the purpose of describing particular embodiments only and is not intended to be limiting to this Disclosure. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

The invention being thus described, it will be obvious that the same may be varied in many ways. Such variations are not to be regarded as departure from the spirit and scope of the invention, and all such modifications as would be obvious to one skilled in the art are intended to be included within the scope of the following claims.

The invention claimed is:

1. A latent fingerprint detection system, comprising:
   a light source;
   a light source alignment portion configured to align the light source at an illumination angle relative to a sample surface, which may possess a latent fingerprint, onto the sample surface such that the light source illuminates the sample surface so that the sample surface produces specular reflection;
   a specular reflection discriminator configured to direct the produced specular reflection to an optical detector aligned relative to the sample surface at an alignment angle that is substantially equal to an angle of reflection of the produced specular reflection such that the directed specular reflection does not saturate the optical detector;
   the optical detector configured to capture the specular reflection from the sample surface and generates image data using essentially only the specular reflection to generate image data of the fingerprint on the sample surface; and
   an image processor configured to analyze the image data of the sample surface to determine if the image data includes the fingerprint by performing slope detection and generate image data of the fingerprint responsive to a determination that the analyzed image data includes the fingerprint.

2. The system of claim 1, further comprising at least one scanner mechanically coupled to the optical detector for scanning the optical detector across a plurality of regions of interest on the sample surface, where the scanner is configured to maintain the alignment angle during scanning.

3. The system of claim 1, wherein the specular reflection discriminator comprises an optical arrangement coupled to the optical detector and where the optical arrangement has a numerical aperture of zero.

4. The system of claim 1, wherein numerical apertures of the light source and the optical detector are substantially equal and opposite.

5. The system of claim 1, wherein the specular reflection discriminator further comprises a partial reflector arranged to direct a portion of illumination from the light source towards the sample surface in a direction perpendicular to the sample surface.

6. The system of claim 1, wherein the specular reflection discriminator further comprises a partial reflector arranged to direct a portion of specular reflection from the sample surface into the optical detector, which is arranged to detect light coming in a perpendicular direction from the sample surface.

7. The system of claim 1, wherein the optical detector comprises an optical arrangement that directs and focuses incoming light onto a detector portion and wherein a numerical aperture of the optical arrangement is zero.

8. A latent fingerprint detection system, comprising:
   a light source alignment portion configured to align a collimated beam of light at an illumination angle relative to a sample surface onto the sample surface to produce specular reflection from the sample surface;
   an optical detector configured to capture the specular reflection from the sample surface to generate image data for use to determine whether a fingerprint is on the sample surface;
   a specular reflection discriminator configured to direct the produced specular reflection to the optical detector aligned relative to the sample surface at an alignment angle that is substantially equal to an angle of reflection of the produced specular reflection such that the directed specular reflection does not saturate the optical detector; and
   an image processor configured to analyze the image data of the sample surface to determine if the image data includes the fingerprint by performing slope detection and generate image data of the fingerprint responsive to a determination that the analyzed image data includes the fingerprint.

9. The system of claim 8, further comprising at least one scanner mechanically coupled to the optical detector for scanning the optical detector across a plurality of regions of interest on the sample surface, where the scanner is configured to maintain the alignment angle during scanning.

10. The system of claim 8, wherein the specular reflection discriminator comprises an optical arrangement coupled to the optical detector and where the optical arrangement has a numerical aperture of zero.

11. The system of claim 8, wherein the specular reflection discriminator further comprises a partial reflector arranged to direct a portion of the collimated beam of light towards the sample surface in a direction perpendicular to the sample surface.

12. The system of claim 8, wherein the specular reflection discriminator further comprises a partial reflector arranged to direct a portion of specular reflection from the sample surface into the optical detector, which is arranged to detect light coming in a perpendicular direction from the sample surface.

13. The system of claim 8, wherein the optical detector comprises an optical arrangement that directs and focuses incoming light onto a detector portion and wherein a numerical aperture of the optical arrangement is zero.

14. A method comprising:
   aligning a light source at an illumination angle relative to a sample surface onto the sample surface to produce specular reflection from the sample surface with a light source alignment portion;
   capturing the specular reflection from the sample surface to generate image data for use to determine whether a fingerprint is on the sample surface with an optical detector;
   directing the produced specular reflection to the optical detector aligned relative to the sample surface at an alignment angle that is substantially equal to an angle of reflection of the produced specular reflection such that the directed specular reflection does not saturate the optical detector with a specular reflection discriminator; and
   analyzing, by an image processor, the image data of the sample surface to determine if the image data includes the fingerprint by performing slope detection and generate image data of the fingerprint responsive to a determination that the analyzed image data includes the fingerprint.

15. The method of claim 14, further comprising scanning the optical detector across a plurality of regions of interest on the sample surface, where the seamier is configured to maintain the alignment angle during scanning with at least one scanner mechanically coupled to the optical detector.

* * * * *